United States Patent [19]

Dureja et al.

[11] Patent Number: 4,622,315

[45] Date of Patent: Nov. 11, 1986

[54] ADDITIVES FOR IMPROVED PESTICIDE PHOTSTABILITY

[75] Inventors: Prem Dureja; John E. Casida; Luis O. Ruzo, all of Berkeley, Calif.

[73] Assignee: The Regents of the University of California, Berkeley, Calif.

[21] Appl. No.: 465,440

[22] Filed: Feb. 10, 1983

[51] Int. Cl.[4] ..................... A01N 65/00; A01N 53/00
[52] U.S. Cl. ..................................... 514/70; 514/531; 514/972; 424/195.1
[58] Field of Search ................ 424/174, 195; 514/972, 514/70, 531

[56] References Cited

U.S. PATENT DOCUMENTS 2,421,223  5/1947  Smith et al. ..................... 424/193
2,772,198  11/1966 Smith et al. ..................... 424/188
4,045,555  8/1977  Ferrari et al. .............. 424/DIG. 12

OTHER PUBLICATIONS

Miskus et al., CA 77:1832z (1972).
Abe et al., CA 78:159008r (1972).
Miskus et al, CA 78:68174a (1972).
Glynn Jones, CA 55:21451h (1960).
Blackith, CA 47:3509f (1952).
Abe et al, CA 81:34588k (1973).
Werner, CA 60:4716h (1963).
Tattersfield et al, CA 29:4477[8] (1934).
Photochem. Reactions of Syn. Pyrethroids, Progress in Pesticide Biochem., vol. 2, p. 1–31, (1982), (Ruzo).
"Pyrethreum Flowers . . . ", (Casida).
"*Environmental Health Perspectives*", vol. 34, pp. 189–202, (1980).
"Stabilization of Bioethanolmethrin . . . ", *J. Agric. Food Chem.*, vol. 30, pp. 405–407 (1982), (Pieper et al.).
"Stabilization of Thin Films . . . ", *J. Agric. Food Chem.*, vol. 20, pp. 313–315 (1972), (Miskus et al).

*Primary Examiner*—Albert T. Meyers
*Assistant Examiner*—F. Abramson
*Attorney, Agent, or Firm*—Fliesler, Dubb, Meyer & Lovejoy

[57]         ABSTRACT

A number of pyrethroid insecticides are photolabile, thus limiting their use outdoors. The non-photolabile pyrethroids often have the disadvantage of lasting too long when used outdoors. Herein, certain toxicologically acceptable compounds are designated which stabilize the normally photolabile pyrethroids and allow them to be used for an extended time period out of doors. The stabilizers have an electron deficient $\pi$ system and serve to decrease the rate of the photochemical decomposition of the pyrethroid at a given light level.

6 Claims, No Drawings

ADDITIVES FOR IMPROVED PESTICIDE PHOTSTABILITY

This invention was made with Government support under Grant No. ES 00049 awarded by the Department of Health and Human Services. The Government has certain rights in this invention.

TECHNICAL FIELD

This invention relates to a composition of matter which has insecticidal activity and has a controllable degree of persistence. The invention further relates to a method of killing insects utilizing such a composition. More particularly, the invention relates to controlling the photostability of pyrethroid insecticides.

BACKGROUND ART

Pyrethrum flowers, their insecticidal pyrethrins component and the other pyrethroid compounds have significant insecticidal activity. Indeed, pyrethrins and pyrethrins-containing plant extracts have been used for such purposes for over a century.

The pyrethroid compounds fall into one of two classes insofar as photostability is concerned. Most of the pyrethroid compounds are decomposed by light, particularly, by ultraviolet light (290 to 320 nm). A few of the pyrethroids are quite stable to light. Those pyrethroids which are very stable to light provide a possible problem in that their use may lead to ingestion of the stable pyrethroids by animals other than insects with resulting potential damage to those animals. The photolabile pyrethroids, on the other hand, are only occasionally used outdoors since they decompose quite readily when exposed to sunlight. It would be advantageous if a pyrethroid composition could be formulated which was sufficiently light stable so as to be usable outdoors and yet which would decompose after a selected time of use outdoors so as to prevent any environmental damage, toxicity problems with higher animals, and the like.

Attempts have been made in the past to stabilize some of the photolabile pyrethroids. These attempts have generally consisted of adding antioxidants and/or light absorbers which act as uv screens in the 290 to 320 nm range (see, for example, Miskus, R. P. and Andrews, T. L., J. Ag. Food Chem. 20, 313–315 (1972); and Pieper, G. R. and Rappaport, N. L., J. Agric. Food Chem. 30, 407–408 (1982)). Another compound which has been used to photostabilize pyrethroids is p-amino azobenzene. This compound has been found to be an effective stabilizer as disclosed in U.S. Pat. No. 2,772,198, issued Nov. 27, 1956. However, many azoaromatic compounds and/or their degradation products are carcinogenic and thus their use is not appropriate since a stabilizer must be toxicologically safe as well as effective. See, for example, "Casarett and Doull's Toxicology: The Basic Science of Poisons", Second Edition, MacMillan Publishing Co., Inc., New York, 1980, as to the carcinogenic properties of azoaromatic compounds.

A better understanding of the pyrethroids and their photochemistry may be obtained by reading a review of the use of pyrethrins and pyrethroid insecticides by J. E. Casida which appears in Environmental Health Perspectives, 34, 189–202 (1980) and a review of the photochemical reactions of the pyrethroids by L. O. Ruzo which appears in Pesticide Biochemistry, Vol. 2, edited by D. H. Hutson and T. R. Roberts, John Wiley & Sons, Ltd., 1982.

While attempts to stabilize photolabile pyrethroids have met with some success, such success has only been sufficient to allow limited outdoor use of normally photolabile pyrethroid insecticides.

DISCLOSURE OF THE INVENTION

This invention is concerned with solving one or more of the problems of the prior art as set forth above.

In accordance with one aspect of the present invention, a composition is provided having insecticidal activity and controllable persistence. The composition comprises a photolabile pyrethroid having insecticidal activity along with an effective amount of a stabilizer which is toxicologically safe, which has an electron deficient $\pi$ system and which decreases the rate of the photochemical decomposition reaction of the pyrethroid at a given light level.

In accordance with another embodiment of the present invention, a method is provided of stabilizing a photolabile pyrethroid insecticide. The method comprises admixing with the pyrethroid an effective amount of a toxicologically safe stabilizer which has an electron deficient $\pi$ system and which significantly decreases the rate of the photochemical decomposition reaction of the pyrethroid.

In accordance with still another embodiment of the present invention, a method is set out of killing insects with an insecticide which is decomposed when exposed to the light for a selected time period during its use. The method comprises admixing a photolabile pyrethroid having an insecticidal effectiveness period in the dark at least as great as the selected time period and in the light significantly less than the selected time period, with an amount of a toxicologically safe stabilizer which decreases the rate of the photochemical decomposition reaction of the pyrethroid sufficiently so that the resultant admixture has an insecticidal effectiveness period when exposed to light during its use equal to the selected time period and exposing insects to the thus obtained admixture.

Pest control requires the use of bioactive chemicals with suitable persistence to protect treated surfaces from pest invasion or attack for several hours or days or to kill insects contacting the treated surfaces. The effectiveness and use areas for a pesticide are often determined by its persistence. A short residual insecticide may be best for one situation and a longer persistence chemical for another pest or use. An ideal situation involves an additive that is generally toxicologically safe and that can be introduced in varying amounts to achieve the desired degree of persistence. Pyrethroids are one type of pesticide where this would be of value. When operating in accordance with the present invention, compositions are provided which have these properties.

BEST MODE FOR CARRYING OUT THE INVENTION

In accordance with the present invention, it has been discovered that certain compounds can be admixed with pyrethroid insecticides which are not photostable to provide insecticidal compositions having a desired degree of photostability. The term "pyrethroid" is used herein to include pyrethrum extract and the natural pyrethrins as well as the synthetic compounds. Many of the additive chemicals are relatively inexpensive, particularly compared to the cost of pyrethroid insecticides. Accordingly, through the use of small amounts of inexpensive toxicologically safe compounds, the effectiveness period of pyrethroids, when exposed to light during their use, can be very significantly increased.

As has been alluded to previously, a useful stabilizer must be toxicologically safe in that it must generally be non-toxic, non-carcinogenic and non-allergenic. The term "toxicologically safe" is used herein to indicate that while the stabilizer may have some toxic, carcinogenic or allergenic property, the degree of such property must be so slight as to cause no significant problem when the stabilizer is used in the manner and in the concentrations contemplated.

The compounds which have been found to be effective in stabilizing photolabile pyrethroid insecticides have certain attributes in common. Most particularly, the useful stabilizers have an electron deficient π system. The preferred stabilizers include an aromatic ring having at least one attached electron withdrawing group and having at least one electron donating group ortho or para to the electron withdrawing group.

The preferred electron withdrawing group is a nitro group. The electron donating group may be an amino or substituted amino group, a hydroxyl group, an alkoxy group, or a phenoxy group. Additional electron donating groups which may substitute for the preferred groups may be determined by reference to the ordinary Hammett substituent constants (The Chemist's Companion, A. J. Gordon and R. A. Ford, John Wiley & Sons, New York, pp 145–147). Generally, the electron withdrawing group should have a σ-para value of at least about 0.3 and the electron donating group should have a σ-para value of no more than about −0.2. More than one electron withdrawing group and/or more than one electron donating group may be present in the stabilizer molecule. The above discussed stabilizers act to decrease the rate of the photochemical decomposition reaction of the pyrethroid at a given light level. The pyrethroid compound generally has a formula representable by:

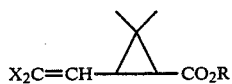

where R may be any of a wide variety of organic radicals and X may be a lower alkyl group, usually a methyl group, CO$_2$CH$_3$, or any of a variety of organic radicals, or a halogen. However, if X is a halogen the pyrethroid will usually be photostable whereby the stabilizers of the present invention will be unnecessary. Examples of photolabile pyrethroids include pyrethrin I, pyrethrin II, jasmolin I, t-resmethrin, t-allethrin, t-phenothrin and kadethrin.

Several factors influence or determine the photostabilizing activity of the stabilizers of the present invention. A photochemical interaction appears to be involved between the pyrethroid and the additive since different yields and/or major reaction products are obtained when the pyrethroid is irradiated with and without the additives. The stabilization provided by the additives serves to decrease the role of the photodecomposition processes. For example, the yield of cyphenothrin epoxide is higher when cyphenothrin is irradiated alone than when it is irradiated in the presence of trifluralin, phenothiazine or 8-hydroxyquinoline. The decrease in oxidation could be caused by competitive photoreactions of the stabilizer with oxygen, but such cannot be the sole factor responsible since stabilization is obtained even at low stabilizer to pyrethroid ratios. Competitive light absorption by the stabilizer is an unlikely possibility since pyrethroids that are fair light absorbers (kadethrin or resmethrin) are also effectively stabilized at very low additive to pyrethroid ratios. Furthermore, many other compounds that are effective light absorbers are not effective stabilizers. Alternative possibilities include trapping of oxygen with subsequent stabilizer regeneration, stabilization of the π system in the isobutenyl group (possibly the major oxidative site) of the pyrethroid, energy transfer quenching by the stabilizer of the excited state leading to oxidation, and electron transfer reactions which may render oxygen less reactive, i.e., by forming superoxide ions. Such factors may be justified by the low excited state energies of these additives and the ring currents they exhibit. The presence of an electron withdrawing group and an ortho or para electron donating group on an aromatic ring causes the ring to become an "electron sink" in which the unpaired oxygen electrons or the pyrethroid's π system may interact. The present invention is not meant in any way to be limited or bound by the theoretical considerations just discussed. However, from the experiments to date, it has become clear that the stabilizer of the present invention interferes directly with, in one way or another, and thereby significantly decreases the rate of the photochemical decomposition reaction of the pyrethroid.

Particularly effective stabilization has been found with the compounds trifluralin, pendimethalin, p-nitrophenol, o-nitrophenetole and 4-nitrocatechol. Of lesser, but still substantial effectiveness, are o-nitrophenol. A number of compounds have been screened which have had little or no effectiveness in stabilizing pyrethroid insecticides. Such compounds include quintozene (PCNB), heptachlor, propoxur, pyrazone, carbaryl, chlorpyrifos, pirimicarb, thioxanthone, benzil, thanite, thayer, pyrene, chrysene, fluorene, benzophenone, endosulphan, lindane, benzoin, mirex, matacil, profenophos, atrazine, dichlone, amitrole, terbacil, hexachlorocyclohexane (BHC), DDT, mesurol, malathion, stilbene, aldrin, kelthane, chlordane, azinphos-methyl (guthion), isoprene, dessin, nitrobenzene, cypermethrin, p-chlorophenol, p-aminophenol, p-nitrobenzoic acid, o-aminophenol, 2,3,6-trichlorophenol, 3-dimethylaminophenol, 2-chloro-5-nitrobenzoic acid, 3,5-dihydroxybenzoic acid, 2,3-dihydroxybenzoic acid, 3-hydroxyflavone, coumaphos, isocoumarin, 2-amino-5-chlorobenzoic acid, p-methylbenzoic acid, p-chlorobenzaldehyde, p-bromoacetophenone, m-nitroacetophenone, 2-coumarone, bis-hydroxy-coumarin, 2-chlorobenzoxazole, 8-hydroxybenzoquinoline, coumarin, phthalimide, maleic anhydride, tetrahydrophthalimide, ethyl chrysanthemate, m-phenoxybenzaldehyde, phthalic anhydride, chlorobenzilate, diquat dibromide, chlorophyll, α-hexachlorocyclohexane, phloroglucinol, p-chlorobenzoic acid.

As will be apparent from the preceding paragraph significant photostabilization is attainable using additives which are monocyclic aromatic compounds having a nitro group attached thereto and having an electron donating group attached to the monocyclic aromatic ring ortho or para to the nitro group, the electron donating group having a Hammet σ-para value of no more than about −0.2.

The amount of the stabilizer added may vary greatly depending upon the desired period of effectiveness for the insecticidal composition. Amounts as little as one part of stabilizer per 100 parts of pyrethroid have considerable stabilizing effect, particularly when the stabilizer chosen is one of the more effective stabilizers, as set out above.

The invention will be better understood by reference to the following illustrative examples which set out actual tests run utilizing various pyrethroids and various stabilizers or potential stabilizers.

EXAMPLE 1

Effects of Various Candidate Stabilizers on Cyphenothrin Photodegradation

The cyphenothrin (10 μg) and the candidate stabilizer (10 μg) were exposed to light for 24 hours (360 nm, Rayonette Reactor) as deposited on pre-coated silica gel plates (EM Reagents, 0.25 mm thickness) obtained by applying appropriate volumes of a chloroform stock solution. The 360 nm Rayonette Reactor was used since the radiation produced by this reactor in the 290 nm–320 nm range approximates the radiation from the sun in that range. The plates were pre-washed with methanol and did not contain fluorescent indicator.

After exposure the plates were developed in either carbon tetrachloride-ether (3:1) or carbon tetrachloride-toluene (1:1) to detect ester cleavage and isomerization products, respectively. The region corresponding to the starting material and its isomers was extracted with ether and analyzed by either electron-capture-gas chromatography or in the case of $^{14}$C-labeled cyphenothrin, by autoradiography followed by liquid scintillation counting. Percent recoveries were determined by comparison of irradiated and dark samples. The results are summarized in Table 1. Similar findings were obtained when samples were irradiated on glass surfaces with sunlight.

TABLE 1

| Effectiveness of various candidate stabilizers on cyphenothrin photodegradation[a] | | | |
|---|---|---|---|
| High Effectiveness (90–100% recovery) | Medium Effectiveness (50–75% recovery) | Little or no effectiveness (<50% recovery) | |
| trifluralin | 8-hydroxyquinoline | quintozene | nitrobenzene |
| pendimethalin | phenothiazine | heptachlor | cypermethrin |
| p-nitrophenol | o-nitrophenol | propoxur | p-chlorophenol |
| o-nitrophenetole | p-cyanophenol | pyrazole | p-aminophenol |
| 4-nitrocatechol | 2,4-dihydroxyacetophenone | carbaryl | p-nitrobenzoic acid |
| | carbazole | chlorpyrifos | o-aminophenol |
| | phenylthiourea | pirimicarb | 2,3,6-trichlorophenol |
| | benzimidazole | thioxanthone | 3-dimethylaminophenol |
| | o-hydroxybenzophenone | benzil | 2-chloro-5-nitrobenzoic acid |
| | triphenylamine | thanite | 3,5-dihydroxybenzoic acid |
| | diphenylamine | thayer | 2,3-dihydroxybenzoic acid |
| | hydroquinone | pyrene | 3-hydroxyflavone |
| | acetophenone | chrysene | coumaphos |
| | chlorobenzilate | fluorene | isocoumarin |
| | rotenone | benzophenone | 2-amino-5-chlorobenzoic acid |
| | chloranil | endosulphan | p-methylbenzoic acid |
| | | lindane | p-chlorobenzaldehyde |
| | | benzoin | p-bromoacetophenone |
| | | mirex | m-nitroacetophenone |
| | | matacil | 2-coumarone |
| | | profenophos | bis-hydroxy coumarin |
| | | atrazine | 2-chlorobenzoxazole |
| | | dichlone | 8-hydroxybenzoquinoline |
| | | amitrole | hexachlorocyclohexane (BHC) |
| | | terbacil | phthalimide |
| | | coumarin | maleic anhydride |
| | | DDT | tetrahydrophthalimide |
| | | mesurol | ethyl chrysanthemate |
| | | malathion | m-phenoxybenzaldehyde |
| | | stilbene | phthalic anhydride |
| | | aldrin | chlorobenzilate |
| | | kelthane | diquat dibromide |
| | | chlordane | azinphos-methyl (guthion) |
| | | chlorophyll | α-hexachlorocyclohexane |
| | | isoprene | phloroglucinol |
| | | dessin | p-chlorobenzoic acid |

[a]Recovery of cyphenothrin without stabilizer was <10%.

The data in Table 1 and as obtained in this example illustrate the very striking effectiveness of the stabilizers in accordance with the present invention, when used in a one to one mixture with a pyrethroid.

EXAMPLE 2

Insect Tests

The pyrethroid (1–300 μg) and the candidate stabilizer, in a ratio of 5 parts pyrethroid to 1 part stabilizer, by weight, were applied onto glass petri dishes and exposed to ultraviolet light (360 nm) for 4 hours. Anaesthetized houseflies were then introduced into the dish, the dish was covered and the 24 hr. LD$_{50}$ value was determined with and without stabilizer. These results are set out in Table 2.

TABLE 2

Enhanced Effectiveness of Resmethrin and Cyphenothrin in Fly Control on Adding One Part Trifluralin to Five Parts Insecticide and Phorodegradation for Four Hours

| | LD$_{50}$ (μg/dish) | | |
|---|---|---|---|
| | Dark | Irradiated | |
| Pyrethroid | control | Control | Trifluralin |
| Resmethrin | 2 | 300 | 8 |
| Cyphenothrin | 4 | 220 | 8 |

This example illustrates the effectiveness of one of the preferred stabilizers of the present invention in stabilizing the pyrethroids resmethrin and cyphenothrin against photodecomposition.

EXAMPLE 3

Effect of Lesser Amounts of Stabilizer

The candidate stabilizers trifluralin, 8-hydroxyquinoline, phenothiazine and p-nitrophenol were tested in various ratios to cyphenothrin utilizing the chemical procedure indicated in Example 1 but limiting the exposure time to 12 hours. The results are set out in Table 3.

This example demonstrates that 60-80% of the cyphenothrin was recoverable after 12 hours' exposure to ultraviolet light at 360 nm even when the stabilizer was present in only one part of stabilizer to 100 parts of cyphenothrin. The cyphenothrin alone, when run in the same test, showed less than 2% recovery. Thus, the high effectiveness of the stabilizer of the present invention is illustrated.

EXAMPLE 4

Tests on Several Pyrethroids

A chemical test as indicated in Example 1 was carried out with the exception that the stabilizer was present in a ratio of one part stabilizer to five parts pyrethroid and that the photodegradation reaction was continued for 18 hours. The pyrethroids kadethrin, allethrin, resmethrin, cyphenothrin and pyrethrum extract, were all tested by this procedure. Table 4 sets out the results of that testing.

TABLE 3

Effect of Stabilizer Concentration on % Recovery of Cyphenothrin After 12 Hours Exposure

| Stabilizer | % Recovery at ratio (cyphenothrin:stabilizer) | | | | | | |
|---|---|---|---|---|---|---|---|
| | 1 | 2 | 3 | 5 | 10 | 50 | 100 |
| Trifluralin | 100 | 100 | 100 | 98 | 95 | 90 | 80 |
| 8-Hydroxyquinoline | 100 | 100 | 100 | 90 | 85 | 80 | 75 |
| Phenothiazine | 100 | 100 | 100 | 85 | 80 | 75 | 60 |
| p-Nitrophenol | 100 | 100 | 100 | 90 | 80 | 75 | 70 |

TABLE 4

Enhanced Stability of Five Pyrethroids on Adding One Part Trifluralin to Five Parts Insecticide and Photodegradation for 18 Hours

| Pyrethroid | % Recovery of pyrethroid | |
|---|---|---|
| | Control | Trifluralin |
| Pyrethrum Extract | 0 | ~30 |
| Kadethrin | 0 | 50 |
| Allethrin | 0 | 80 |
| Resmethrin | <5 | 90 |
| Cyphenothrin | 5 | 98 |

The trifluralin stabilizer tested provided very significant stabilization for all of the pyrethroids, more particuarly for the allethrin, resmethrin and cyphenothrin pyrethroids. Accordingly, this example confirms the broad applicability of the stabilizers of the present invention to different photolabile pyrethroids.

Industrial Applicability

The invention operates to provide an insecticidal composition of controllable persistence. It also allows pyrethroids to be effectively utilized for relatively long periods outdoors which have previously only been effectively utilized for short periods outdoors. Furthermore, the stabilizers of the present invention can be used with pyrethroid synergists.

While the invention has been described in connection with specific embodiments thereof, it will be understood that it is capable of further modifications, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A composition having insecticidal activity and controllable persistence, comprising:
    a photolabile pyrethroid having insecticidal activity; and
    an effective amount of a toxicologically safe stabilizer which significantly decreases the rate of the photochemical decomposition reaction of the pyrethroid at a given light level, the stabilizer having an electron deficient $\pi$ system, said stabilizer having a monocyclic aromatic ring with an attached nitro group and with an electron donating group ortho or para to the nitro group, said electron donating group being an amino or substituted amino group, a hydroxyl group, an alkoxy group or a phenoxy group.

2. A composition having insecticidal activity and controllable persistence, comprising:
    photolabile pyrethroid having insecticidal activity; and
    an effective amount of a toxicologically safe stabilizer which significantly decreases the rate of the photochemical decomposition reaction of the pyrethroid at a given light level, the stabilizer having an electron deficient $\pi$ system which includes a monocyclic aromatic ring with an attached nitro group and with an attached electron donating group ortho or para to the nitro group, said electron donating group having a Hammett $\sigma$-para value of no more than about $-0.2$.

3. A composition having insecticidal activity and controllable persistence, comprising:
    a photolabile pyrethroid having insecticidal activity; and
    an effective amount of a toxicologically safe stabilizer which significantly decreases the rate of the photochemical decomposition reaction of the pyrethroid at a given light level, the stabilizer having an electron deficient $\pi$ system and being selected from the group consisting of trifluralin, pendimethalin, p-nitrophenol, o-nitrophenetole, 4-nitrocatechol and o-nitrophenol.

4. A method of killing insects with a pyrethroid which is decomposed when exposed to light for a selected time period during its use, comprising:
    admixing a photolabile pyrethroid having an insecticidal effectiveness period in the dark of at least as great as said selected time period and when exposed to light of significantly less than said selected time period with an amount of a toxicologically safe stabilizer which decreases the rate of the photochemical decomposition reaction of the pyrethroid sufficiently so that the resultant admixture has an insecticidal effectiveness period when exposed to light during its use equal to said selected time period, said stabilizer having a monocyclic aromatic ring with an attached nitro group and with an electron donating group ortho or para to the nitro group, said electron donating group being an amino or substituted amino group, a hydroxyl group, an alkoxy group or a phenoxy group; and exposing insects to said admixture.

5. A method of killing insects with a pyrethroid which is decomposed when exposed to light for a selected time period during its use, comprising:
admixing a photolabile pyrethroid having an insecticidal effectiveness period in the dark of at least as great as said selected time period and when exposed to light of significantly less than said selected time period with an amount of a toxicologically safe stabilizer which decreases the rate of the photochemical decomposition reaction of the pyrethroid sufficiently so that the resultant admixture has an insecticidal effectiveness period when exposed to light during its use equal to said selected time period, said stabilizer having a monocyclic aromatic ring with an attached nitro group and an attached electron donating group ortho or para to the nitro group, said electron donating group having a Hammet $\sigma$-para value of no more than about $-0.2$; and
exposing insects to said admixture.

6. A method of killing insects with a pyrethroid which is decomposed when exposed to light for a selected time period during its use, comprising:
admixing a photolabile pyrethroid having an insecticidal effectiveness period in the dark of at least as great as said selected time period and when exposed to light of significantly less than said selected time period with an amount of a toxologically safe stabilizer which decreases at the rate of the photochemical decomposition reaction of the pyrethroid sufficiently so that the resultant admixture has an insecticidal effectiveness period when exposed to light during its use equal to said selected time period, said stabilizer being selected from the group consisting of trifluralin, pendimethalin, p-nitrophenol, o-nitrophenetole, 4-nitrocatechol and o-nitrophenol; and
exposing insects to said admixture.

* * * * *